United States Patent [19]
Merva

[11] Patent Number: 4,969,111
[45] Date of Patent: Nov. 6, 1990

[54] OIL PERMEAMETER AND METHOD OF MEASURING HYDRAULIC CONDUCTIVITY

[75] Inventor: George E. Merva, East Lansing, Mich.

[73] Assignee: Tresco, Incorporated, Spring Lake, Mich.

[21] Appl. No.: 283,250

[22] Filed: Dec. 12, 1988

[51] Int. Cl.$^5$ ...................... G01L 11/00; G01N 15/08
[52] U.S. Cl. ..................................... 364/556; 364/422; 73/73; 340/604; 324/694
[58] Field of Search ............... 364/550, 556, 569, 422; 340/602, 604, 618; 73/73, 74, 76, 298, 323; 324/61 R, 65 R

[56] References Cited

U.S. PATENT DOCUMENTS

| | | | |
|---|---|---|---|
| 4,332,172 | 6/1982 | Torstensson | 73/73 |
| 4,622,643 | 11/1986 | Dotson | 364/556 |
| 4,628,468 | 12/1986 | Thompson et al. | 364/556 |
| 4,638,447 | 1/1987 | Odeh | 364/556 |
| 4,779,200 | 10/1988 | Bradbury et al. | 364/422 |

OTHER PUBLICATIONS

"The Guelph Permeameter for Measuring the Field-Saturated Soil Hydraulic Conductivity Above the Water Table: I. Theory, Procedures and Applications", Proceedings of the Canadian Hydrology Symposium at Quebec City, Quebec, 1984.
"The Guelph Permeameter for Measuring the Field-Saturated Soil Hydraulic Conductivity Above the Water Table: II. The Apparatus", Proceedings of the Canadian Hydrology Symposium at Quebec City, Quebec, 1984.
Exhibit A, Declaration of Dr. George E. Merva dated 4/19/89, "Falling Head Permeameter for Field Investigation of Hydraulic Conductivity", Distributed at National Meeting of the American Society of Agricultural Engineers, 1978.
Exhibit B, Declaration of Dr. George E. Merva dated 4/19/89, "Report and Preliminary Recommendations of Investigation of Zelanka Nursery Site", provided at least to officials of Muskegon Waste Water Authority, Nov., 1985.
Exhibit C, Declaration of Dr. George E. Merva dated 4/19/89, "Soil Core Analysis Zelenka Nursery Property, Muskegon Waste Water Treatment Facility", provided to least of officials of Muskegon Waste Water Authority, Feb. 19, 1986.

Primary Examiner—Parshotam S. Lall
Assistant Examiner—Brian M. Mattson
Attorney, Agent, or Firm—Price, Heneveld, Cooper, DeWitt & Litton

[57] ABSTRACT

A soil permeameter and method of measuring soil conductivity utilizes a core device that is open at one end that is inserted a measure depth into the soil to be tested. A vertically elongated measuring column is connected to the core device and both are supplied with water sufficiently to develop a pressure head in the column. A timer and a data storage device responsive to the timer are provided to measure and store the time intervals for the level of liquid in the column to fall equal increments. The value of soil conductivity is calculated as a function of the depth of core insertion and the stored time intervals. Both horizontal and vertical components of soil conductivity can be determined separately.

19 Claims, 4 Drawing Sheets

OIL PERMEAMETER AND METHOD OF MEASURING HYDRAULIC CONDUCTIVITY

BACKGROUND OF THE INVENTION

This invention is related to a method and apparatus for measuring the hydraulic conductivity, or permeability, of soil, and in particular, to a method and apparatus of the type that develops a head pressure from a column of liquid, such as water, above the soil to be tested and monitors the fall of the liquid head as the liquid soaks into the soil.

A long-felt, unfulfilled need has existed for a fast and accurate technique for measuring soil permeability. Such information is important in many industries. In agriculture, it is necessary in order to properly establish irrigation and drainage systems. In the construction industry, knowledge of soil conditions is important in establishing road drainage. In the home building industry, septic systems are located on the basis of the ability of the soil to "perk".

A conventional technique for measuring soil permeability is to dig a hole at the test site, fill it with water and monitor the time for the water to penetrate into the soil. Such a test is satisfactory for certain applications but is inherently inaccurate especially at extreme values of permeability and is very slow. If the soil is hard clay, the water may take several days to fully saturate into the soil. To improve the degree of accuracy, several techniques have been proposed. In one such technique, a column of water is established above the soil to be tested and a constant head pressure is maintained as water from the column soaks into the soil. The amount of water per unit of time that passes into the soil is measured and hydraulic conductivity is calculated from a known algorithm. While this technique provides a more accurate result than the conventional technique, it is equally slow, taking anywhere from one hour to two or three days to complete, and requires complicated calculations to arrive at a value of hydraulic conductivity. Furthermore, the value is a combined vertical and horizontal conductivity number with no means for separating the horizontal from the vertical components.

SUMMARY OF THE INVENTION

Accordingly, it is an object of the present invention to provide a method and apparatus for measuring soil conductivity that is both fast and accurate. It is a further object of the invention to provide such a method and apparatus that will separately measure horizontal and vertical components of soil conductivity and do so over a much larger range of conductivity values than before possible. The method according to the invention is easy to perform and eliminates the need to measure head pressure values, which can easily be erroneously performed. Furthermore, the present invention provides a measure of statistical validity of its test results in order to determine if the test was correctly performed.

The apparatus according to the present invention utilizes very little water. A two gallon container that may be carried to the test site is sufficient for several hours of operation of the apparatus. Because a test may be typically performed in fifteen minutes, the two gallon supply will be sufficient for many such tests.

Hydraulic conductivity is measured according to the present invention by measuring the rate of change of head pressure of a liquid column connected with the soil in a unique manner. The rate of change of head, or velocity of fall of the water column, is the only variable to be monitored, without regard for the absolute value of the head pressure.

A method of measuring hydraulic conductivity of soil according to the present invention includes providing a core device having a cylindrical wall that is sealed at one end and open at the opposite end. The open end of the core is inserted into the soil a measured depth. The core is hydraulically connected with a measuring column and a source of liquid. The core and column are filled from the liquid source sufficiently to develop a head of liquid in the column. Timing means and data storage means are provided and as liquid from the column passes through the core into the soil, the time intervals between successive, substantially equal, changes in the liquid head are measured and stored. The hydraulic conductivity of the soil being tested is then determined as a function of the stored intervals and the depth that the core is inserted into the soil.

An apparatus for measuring the hydraulic conductivity of soil according to the present invention includes a core device having a cylindrical wall that is sealed at one end and open at the other. The core device is connected by connecting means with a source of liquid and with a vertically oriented elongated measuring column. Input means are provided for allowing a user to specify the distance that the core device is inserted into the soil to be tested, and measuring means are provided for measuring the time intervals between successive, substantially equal, changes in the liquid head as liquid soaks into the soil being tested. Calculating means are provided that are responsive to the measuring means and the input means for calculating the hydraulic conductivity of the soil being tested as a function of the measured time intervals and the inputted measured insertion distance of the core device.

These and other related objects, advantages, and features of this invention will become apparent upon review of the following specification in conjunction with the drawings.

BRIEF DESCRIPTION OF THE DRAWINGS

FIG. 6 is a sectional view taken along the lines VI—VI in FIG. 1.

DESCRIPTION OF THE PREFERRED EMBODIMENT

Figure 1:
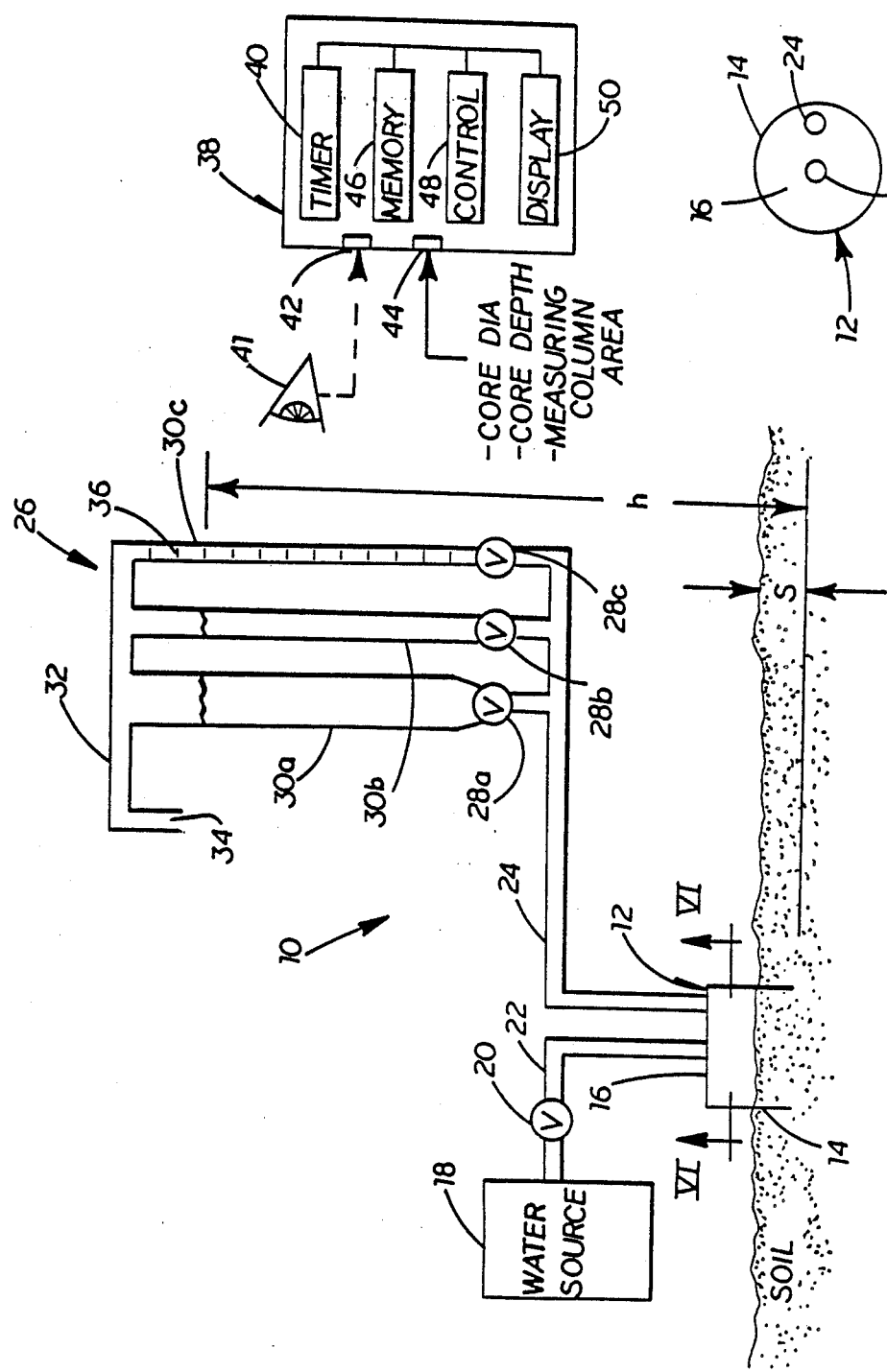
FIG. 1 is a diagram of an apparatus according to the invention.

Referring now specifically to the drawings, and the illustrative embodiments depicted therein, the present invention is based on Darcy's law for soil conductivity:

$$v = -K \frac{h}{x} \tag{1}$$

where:

"h" is the head of a column of water established in contact with the soil,

"x" is the distance of penetration of liquid into the soil,

"v" is the velocity of the liquid penetration, and

"K" is the liquid conductivity.

In the present invention, a soil permeameter generally illustrated as 10 (FIG. 1) includes a core device 12 having a cylindrical wall 14 (FIG. 6) and an end member 16 closing one end of the core device. The end of the core device opposite end member 16 is open such that wall 14 may be inserted into the soil to be tested a measured distance illustrated as S.

Core device 12 is connected with a pressurized source of water 18, such as a tank used with a conventional insecticide sprayer, by a connecting means 22 including a normally closed two-way valve 20. Core device 12 is connected by connecting means 24 to a measuring column assembly illustrated as 26 through valves 28a, 28b, and 28c. Measuring column assembly 26 includes a plurality of vertically oriented elongated measuring columns 30a, 30b, and 30c. Columns 30a–30c are interconnected at their upper end by an overflow tube 32 which includes an opening 34.

When valve 22 and one or more valves 28a–28c are open, water flows from source 18 to fill the portion of core device 12 above the soil level with water and, because water source 18 is pressurized, produces a column of water to height h in the tube or tubes whose corresponding valve 28 is open. When valve 22 is closed, water source 18 is disconnected from core device 12 and the column of water in one or more of the measuring tubes 30 creates a head pressure on the liquid in core device 12 tending to cause the liquid to soak into the soil. Because the core device includes cylindrical wall 14, the liquid may penetrate only the soil within the wall and may not initially penetrate in a direction other than along the axial direction of the cylinder defined by wall 14.

With the apparatus illustrated in FIG. 1, Darcy's law becomes:

$$v = -K \frac{h}{s} \quad (2)$$

Taking the derivative of equation 2 with respect to the parameter h, or head, gives:

$$\frac{dv}{dh} = -\frac{K}{S} \quad (3)$$

which may be rearranged as:

$$K = -S \frac{dv}{dh}. \quad (4)$$

Since it is known that the head velocity is equal to the change in head with respect to time, $$dv \approx \frac{\Delta h_1}{\Delta t_1} - \frac{\Delta h_2}{\Delta t_2} \quad (5)$$

if it is assumed that delta h is kept constant, then $$\frac{dv}{dh} = \frac{1}{t_1} - \frac{1}{t_2} \quad (6)$$

combining equations 4 and 6, an expression for K, or hydraulic conductivity, gives:

$$K = S\left(\frac{1}{t_2} - \frac{1}{t_1}\right). \quad (7)$$

An examination of equation 7 reveals that the hydraulic conductivity is a function of the parameter S which is the depth that core device 12 is inserted into the test soil, and $t_1$ and $t_2$. Since $t_1$ and $t_2$ represent the time interval that it requires the head to drop by an amount h, equation 7 requires the timing of the rate of drop of the liquid head in the connected columns 30. However, equation 7 is completely independent of the absolute value of h. In the illustrative embodiment, the values of $t_2$ and $t_1$ are obtained by applying a plurality of equally spaced marks 36 on one column 30c, which is considered the monitoring column and is always selected to be utilized in each test by opening its valve 28c. The wall of tube 30c, upon which the marks 36 are placed, is transparent so that the head of liquid within tube 30c may be observed as it falls. Thus, $t_1$ and $t_2$ represent the time interval that the head of liquid in tube 30c falls between two marks 36. In performing a test, however, more than just one interval is measured. In fact, the time interval that it takes the head to fall from each mark 36 to the next mark is measured and is expressed as $t_i$ for i=1 through n, where n is the number of intervals.

Figure 2:
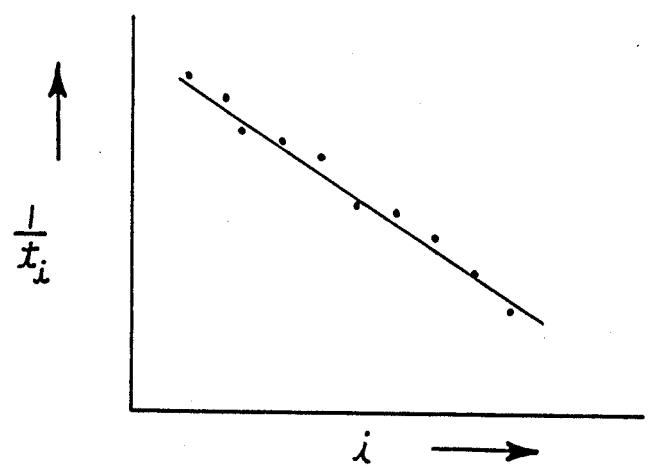
FIG. 2 is a graph illustrating the relationship between successive measured time intervals.

Referring to FIG. 2, when $$\frac{1}{t_i}$$

is plotted for successive values of i, a substantially line is produced whose slope is proportional to K. Therefore, by measuring the time interval between successive equally spaced head increments and determining the slope of the $$\frac{1}{t_i}$$

vs i line, one only needs to multiply the results by the depth of penetration S of the core device to obtain the value for the hydraulic conductivity.

In order to make such time measurements, a computing device 38 is provided having internal timing means 40 and input means 42, such as a key switch operable by a user 41 observing the monitoring column 30c and pressing the key at the occurrence of the head passing each mark 36. Computing device 38 additionally includes second input means 44 for the user to input the diameter of the core device 12, the depth of core device insertion S, and combined cross-sectional areas of the measuring column or columns 30 that are being utilized in the test. The purpose of the multiplicity of columns 30 is in order to allow a gross control over the rate of drop in liquid head by allowing the user to increase the flow by opening additional valves 28, if the head level is dropping too slowly, or closing additional valves 28 if the head is dropping too rapidly for accurate measurements. However, for all tests, tube 30c, which is the monitoring tube, is connected to connecting means 24 by its valve 28c being open. The opening of selected valves 28a–28c is coordinated to occur simultaneously. In the illustrated embodiment, marks 36 are spaced at 1-3 centimeter increments and the preferred rate of head drop is 2-3 seconds per increment. Approximately 6-10 increment measurements should be sufficient to insure an accurate test even with some error in entry of the precise coincidence between the liquid head in tube 30c and any particular mark 36. Measuring column assembly 26 is set up to provide an approximate 150 cm of initial head pressure.

Computing device 38 additionally includes memory means 46 for storing the time values inputted for each mark 36 and a control 48 for coordinating the various functions of the computing device and calculating the value of the hydraulic conductivity. A display 50 is provided to inform the user of the test results. Additional output means, such as a printer (not shown) may additionally be provided to display the results. In the illustrated embodiment, computing device 38 is a hand-held computer that is commercially available and is sold under Model No. 41CX by Hewlett Packard Company. The computer accepts up to four two-kilobyte programmed ROM chips which provides approximately 350 program steps per chip. Only one such ROM chip is required in permeameter 10. In the illustrated embodiment, measuring column 30a has a nominal I.D. of seven-sixteenths of an inch, column 30b has a nominal I.D. of one-quarter of an inch, and column 30c has a nominal I.D. of one-eighth of an inch. Several core devices 12 may be provided having different diameters of wall 14 ranging from 1.61 inches to 4.5 inches in order to accommodate various soil types. The core diameter is much greater than the cross sectional area of the column 30 to enable the fall of the liquid to be sufficiently rapid to allow the user 41 to make accurate observations. The diameter of wall 14 is inputted into computing device at input 44 and is utilized to obtain a ratio by dividing the total cross sectional area within wall 14 into the cross sectional area of the tubes. This ratio is used in calculating the value of hydraulic conductivity. The several core devices 12 may further include various lengths of wall 14 to provide flexibility in inserting core 14 to various soil depths.

Figure 4A:
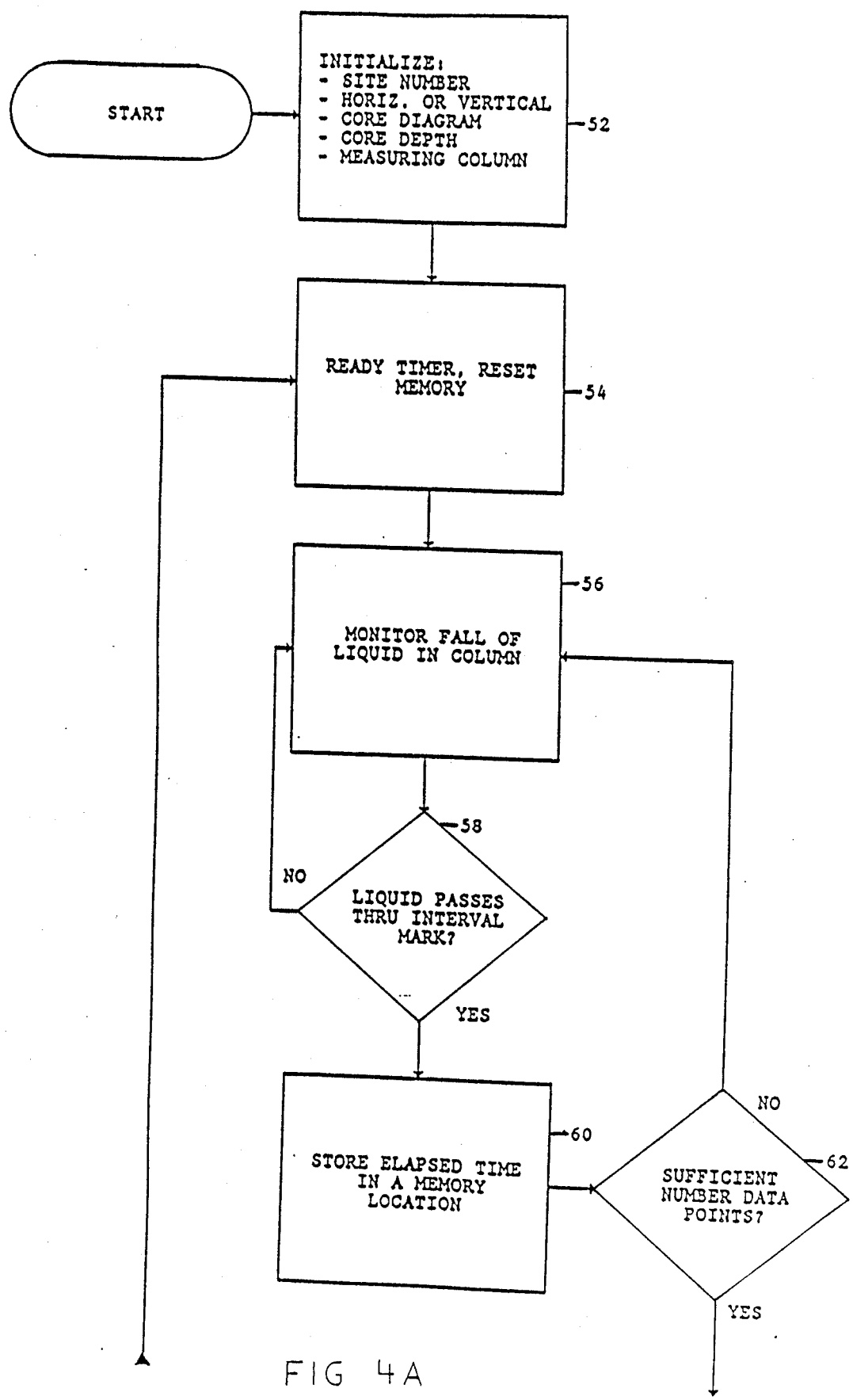
FIGS. 4A–4B are flow diagrams of the software used to implement the invention.
Figure 4B:
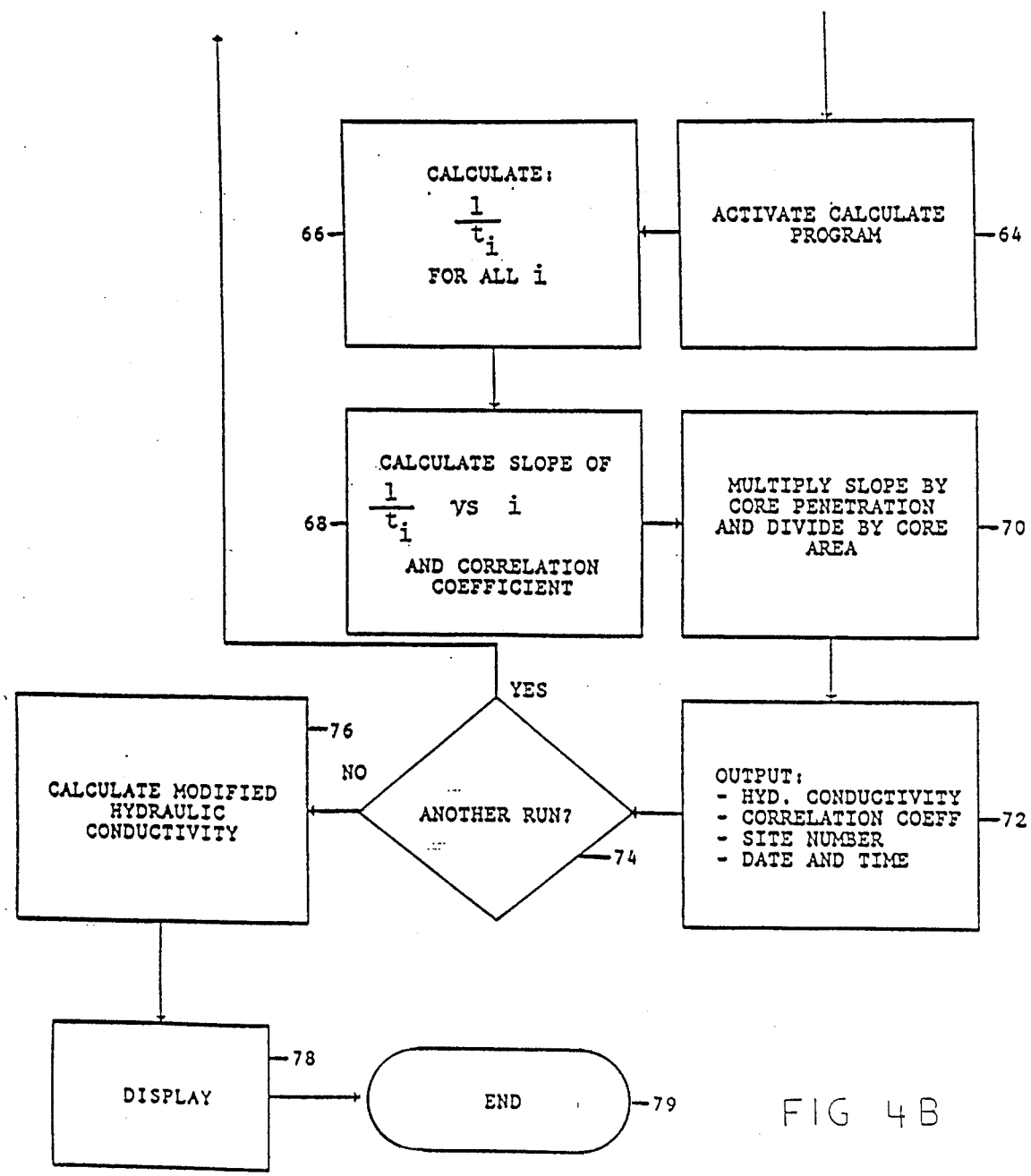

Referring to FIGS. 4A-4B, the present software in computing device 38 is started 51 by initializing at 52 various information input by the user through input means 44. In addition to the measuring column cross-sectional area, core device diameter and penetration, computing device accepts various status information, such as the site number and whether the test is taken with core device 12 in the horizontal or vertical orientation. The software then resets the time interval values at all locations within memory 46 to zero. The software responds at 56 to keystrokes of the user 41 at input 42 as the user observes the liquid level in column 30c passing through each equally spaced mark 36. The software determines at 58 if input key 42 is being pressed. If it is not, then control passes back to 56. If input key 42 is being pressed, the time elapsed in timer 40 since the last stroke of key 42 is determined at 60 and is stored in a suitable location in memory 46. The software then determines at 62 if a sufficient number of data points have been recorded to provide a valid test. If not, control returns to block 56 for further data entry. If a sufficient number of data points have been recorded, then control passes to block 64 where the program to calculate the soil conductivity is activated. Control then passes to blocks 66 where the value of $$\frac{1}{t_i}$$

is calculated for all values of i and passes to block 68 where the slope of the $$\frac{1}{t_i}$$

vs i curve is calculated. Additionally, the software at 68, by conventional, statistical techniques, whether the data points are statistically valid by calculating a correlation coefficient. Control then passes to block 70 where the slope calculated in block 68 is multiplied by the value of core penetration and is multiplied by the ratio of the cross-sectional area of column 36 to that of core 12, both parameters having been entered by the user prior to the test through input 44. Control then passes to block 72 where the calculated value of hydraulic conductivity, the correlation coefficient, the site number and the date and time of the test are written to a memory store or an output device. Control then passes to block 74 where it is determined whether another run is to be made. If so, then control passes back to block 54 where the time values in memory 46 are zeroed in preparation for an additional test. If it is determined at block 74 that all of the tests have been run at that particular site, control then passes to block 76 where a modified hydraulic conductivity value, taking into account all of the tests run at the particular site, is calculated in a manner that will be explained in detail below. The output of hydraulic conductivity determined in block 76 is displayed on display 78 or is provided to any suitable output device.

Figure 3:
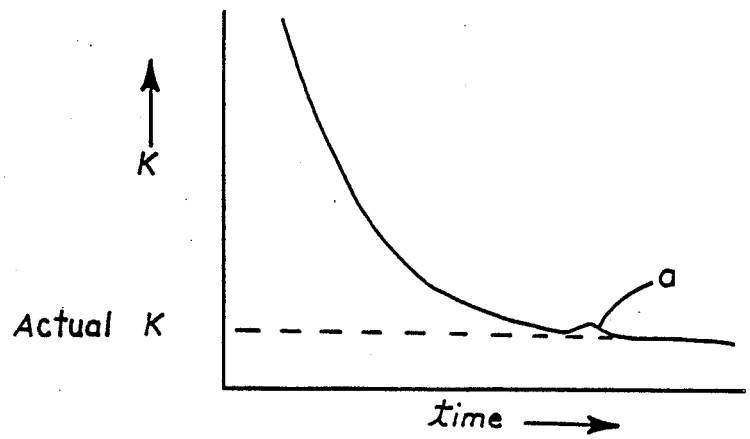
FIG. 3 is a graph illustrating the relationship between successive conductivity values determined according to the invention over a period of time.

According to an aspect of the invention, the conductivity value determined by the apparatus illustrated in FIG. 1 will decrease during successive tests as the wetting front penetrates further into the soil within core device 12. This relationship is illustrated in FIG. 3. It may be observed that the decrease in the conductivity is time dependent because the penetration of the test liquid into the soil will continue between tests. The conductivity curve will eventually become somewhat asymptotic with the time coordinate but may experience a slight positive upward blip at point A when the wetting front has passed through the entire soil core device and has escaped into the soil mass. It is at this pseudo asymptotic point A that the most accurate measure of conductivity is provided and is determined in FIG. 4 by block 76.

Figure 5:
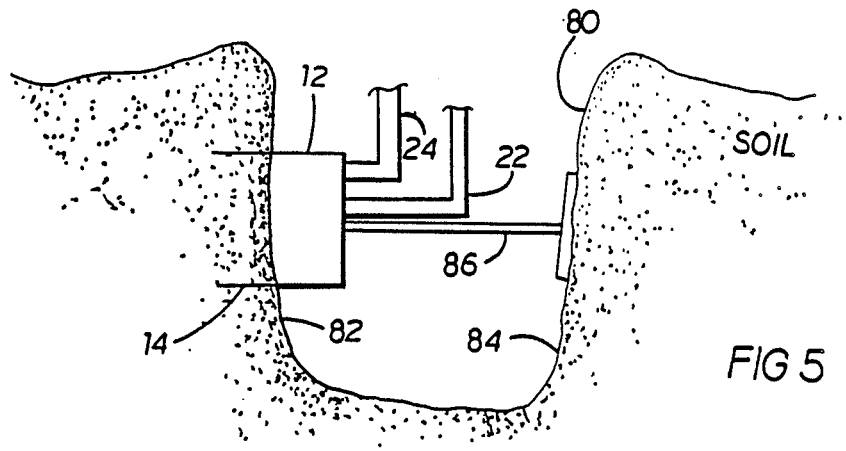
FIG. 5 is a side sectional view of the invention being utilized to measure the horizontal component of the hydraulic conductivity of soil.

Because the present invention provides a controlled wetting front, the direction of penetration of the soil may likewise be controlled. FIG. 5 illustrates a test configuration for measuring soil conductivity in the horizontal direction. To perform such measurement, a trench 80 is dug in the test soil having a pair of generally vertically oriented side walls 82 and 84. Core device 12 is penetrated into one wall 82 by the use of a jack screw 86 extending horizontally between core device 12 and wall 84. The remainder of the apparatus is configured as illustrated in FIG. 1, and the test is conducted as previously described. The only difference is that the user indicates to the computing device that a horizontal measurement is being made for record keeping purposes. Otherwise, the test is the same.

By providing the ability to separately measure vertical and horizontal conductivity components, the present invention provides a much better understanding of soil conditions because various factors, such as cracking due to dry soil conditions, tend to have a much different effect on the horizontal conductivity component than on the vertical conductivity component.

In the illustrated embodiment, a user observes the falling liquid level in measuring column 30c and enters a keystroke at input 42 when the level passes each mark 36. This is a preferred embodiment because it is felt that the intimate involvement of the user provides the user with a better understanding of the capabilities of the apparatus. However, the present invention is capable of implementation by more automated means and the monitoring of time intervals may be accomplished by the mounting of photosensors or electrical conductivity sensors at equally spaced intervals along the measuring column. Other changes and modifications in the specifically described embodiments can be carried out without departing from the principles of the invention which is intended to be limited only by the scope of the appended claims, as interpreted according to the principles of patent law including the doctrine of equivalents.

The embodiment of the invention in which an exclusive property or privilege is claimed are defined as follows:

1. A method of measuring hydraulic conductivity of soil comprising the steps of:
   (a) providing a core device having a cylindrical wall, a member sealing one end of said wall, said wall defining an opening opposite said member;
   (b) inserting said wall of said core device in a direction of said opening a measured depth into the soil being tested;
   (c) providing a measuring column and connecting said core device with said measuring column such that said column extends above said core device;
   (d) providing a timing means for measuring intervals of time and data storage means for storing a plurality of values of said intervals of time;
   (e) filling said core device and said column connected thereto with liquid from a source of liquid until a head of liquid is developed in said column that is above said core device and is capable of forcing liquid in said core device into the soil being tested;
   (f) disconnecting from the source of liquid said core device and measuring column in which said head of liquid has been developed and thereby causing said head of liquid in said column to drop as said head forces liquid in said core into the soil being tested;
   (g) measuring with said timing means the intervals of time between successive substantially equal changes in head in the falling head of liquid as liquid penetrates the soil being tested and storing said intervals of time in said data storage means; and
   (h) determining the hydraulic conductivity of the soil being tested as a function of said intervals of time in said data storage means, and said measured depth independently of absolute values of said head of liquid.

2. The method of claim 1 including performing multiple measurements of hydraulic conductivity by repeating steps e through h a plurality of times and recording the time of day that each of said measurements is made to obtain a plurality of values of hydraulic conductivity and the time of day that each of said values of hydraulic conductivity is measured and determining a composite value of hydraulic conductivity of the soil being tested as a function of variations in said values of hydraulic conductivity with respect to the associated times of day.

3. The method of claim 1 further including comparing each of said intervals of time in said data storage means with other ones of said intervals and determining therefrom a measure of statistical validity of said hydraulic conductivity.

4. The method of claim 1 in which said step c includes providing a plurality of measuring columns and selectivity connecting certain ones of said measuring columns with said core device in order to produce a rate of drop in liquid head during step f that is considered desirable to an operator.

5. The method of claim 1 in which said step c includes providing a transparent surface on said measuring column and equally spaced head markings along said measuring column on said transparent surface; and in which said step g includes observing said head of liquid through said transparent surface and operating said timing means when the head of liquid passes ones of said markings.

6. The method of claim 5 in which said step c further includes providing a plurality of measuring columns and selectively connecting certain ones of said measuring columns with said core device in order to produce a rate of drop in liquid head during step f that is considered desirable to an operator.

7. The method of claim 1 in which said step b includes inserting said wall of said core device into the soil being tested in a substantially vertical orientation.

8. The method of claim 1 in which said step b includes inserting said wall of said core device into the soil being tested in a substantially horizontal orientation.

9. The method of claim 1 in which said step a includes providing a plurality of said core devices having different wall diameters and selecting one of said core devices based on observable characteristics of the soil to be tested; and in which said step h includes determining the hydraulic conductivity of the soil being tested as a function of the diameter of said one of said core devices.

10. The method of claim 1 in which said step h includes determining said hydraulic conductivity according to the relationship:

$$K = S\left(\frac{1}{t_2} - \frac{1}{t_1}\right)$$

where
   K is said hydraulic conductivity;
   S is said measured depth that said core device is inserted into the soil being tested;
   $t_1$ is one of said intervals of time; and
   $t_2$ is another one of said intervals of time.

11. An apparatus for measuring hydraulic conductivity of soil comprising:
   a core device having a cylindrical wall and a member sealing one end of said wall, said wall defining an opening opposite said member adapted to be inserted into soil being tested;
   input means for allowing a user to specify a penetration depth that said core device is penetrated into the soil being tested;
   an elongated measuring column having wall means adapted to hold a liquid when said measuring column is oriented with its elongated dimension substantially vertical and extending above said core;

connecting means for connecting said core device with said measuring column such that liquid in said measuring column forces liquid in said core device through said opening into soil being tested;

means for selectively connecting said core device and measuring column with a source of liquid in order to fill said core device with liquid and establish a head of liquid in said measuring column and for selectively disconnecting said source of liquid from said core device and measuring column such that said head of liquid in said measuring column will drop as liquid permeates the soil being tested;

measuring means for determining intervals of time between successive substantially equal changes in the head of liquid as liquid permeates the soil being tested, said measuring means includes timing means for measuring intervals of time, second input means for establishing beginnings and ends for said intervals in response to said head of liquid dropping substantially equal amounts and data storage means for storing values of said intervals of time; and calculating means responsive to said measuring means and said input means for calculating the hydraulic conductivity of the soil being tested as a function of said intervals of time in said data storage means and said penetration depth and independent of absolute values of said head of liquid.

12. The apparatus of claim 11 in which said calculating means further includes comparing means for comparing each of said intervals of time in said data storage means with other ones of said intervals of time and means responsive to said comparing means for determining statistical validity of said hydraulic conductivity.

13. The apparatus of claim 12 including a plurality of measuring columns and valve means for selectively connecting said columns with said core device in order to allow a user to select a rate of drop of liquid in said measuring columns.

14. The apparatus of claim 11 in which said wall means includes a transparent portion and equally spaced markings along said measuring column on said transparent portion and in which said second input means includes means for allowing a user observing liquid through said transparent portion to indicate when the head of liquid drops to one of said markings, said timing means being responsive to said second input means for establishing beginnings and ends to said intervals of time.

15. The apparatus of claim 14 including a plurality of measuring columns and valve means for selectively connecting said columns with said core device.

16. The apparatus of claim 11 including a plurality of said core devices having different wall diameters, said core devices being selectively connectable individually with said measuring column by said connecting means.

17. The apparatus of claim 16 in which said input means includes means for allowing a user to designate one of said core devices being connected with said measuring column.

18. The apparatus of claim 17 in which said core devices have different wall lengths.

19. The apparatus of claim 11 in which said calculating means includes means for calculating said hydraulic conductivity according to the relationship:

$$K = S\left(\frac{1}{t_2} - \frac{1}{t_1}\right)$$

where
K is said hydraulic conductivity;
S is a value of said penetration depth entered in said input means;
$t_1$ is one of said intervals of time stored in said data storage means; and
$t_2$ is another one of said intervals of time stored in said data storage means.

* * * * *

UNITED STATES PATENT AND TRADEMARK OFFICE
CERTIFICATE OF CORRECTION

PATENT NO. : 4,969,111
DATED : November 6, 1990
INVENTOR(S) : George E. Merva

It is certified that error appears in the above-identified patent and that said Letters Patent is hereby corrected as shown below:

Column 4, line 1, after "6" delete --,,--.

Column 4, line 1, after "6" insert --to obtain--.

Column 6, line 11, after "software" insert --determines--.

Column 8, line 9 & 10, "selectivity" should be --selectively--.

Signed and Sealed this

Twenty-first Day of April, 1992

Attest:

HARRY F. MANBECK, JR.

*Attesting Officer*  *Commissioner of Patents and Trademarks*